(12) United States Patent
Lewis et al.

(10) Patent No.: US 11,597,950 B1
(45) Date of Patent: Mar. 7, 2023

(54) SYSTEMS, COMPOSITIONS, AND METHODS OF FERMENTATION WITH Z. MOBILIS

(71) Applicant: POET Research, Inc., Sioux Falls, SD (US)

(72) Inventors: Stephen M. Lewis, Sioux Falls, SD (US); Benjamin P. Gacke, Baltic, SD (US); Jennifer Rebecca Headman, Sioux Falls, SD (US); Neelakantam V. Narendranath, Fort Mill, SC (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 17/198,154

(22) Filed: Mar. 10, 2021

Related U.S. Application Data

(60) Provisional application No. 62/988,050, filed on Mar. 11, 2020.

(51) Int. Cl.
*C12P 7/06* (2006.01)

(52) U.S. Cl.
CPC .............. *C12P 7/06* (2013.01); *C12Y 301/03* (2013.01); *C12Y 302/01004* (2013.01); *C12Y 302/01008* (2013.01)

(58) Field of Classification Search
CPC . C12P 7/06; C12Y 301/03; C12Y 302/01004; C12Y 302/01008
See application file for complete search history.

(56) References Cited

U.S. PATENT DOCUMENTS

| 8,759,069 B2 | 6/2014 | Fox et al. |
| 2010/0093050 A1 | 4/2010 | Hakalehto et al. |
| 2019/0323041 A1 | 10/2019 | Rasmussen et al. |

FOREIGN PATENT DOCUMENTS

| CN | 102160595 | 12/2012 |
| CN | 103609985 | 10/2013 |
| CN | 106520584 | 10/2019 |
| JP | H0888572 | 1/1996 |
| WO | WO 2010/096673 | 8/2010 |
| WO | WO 2013090053 | 12/2012 |
| WO | WO 2020100072 | 11/2019 |

OTHER PUBLICATIONS

Abate et al., Ethanol production by a mixed culture of flocculent strains of Zymomonas mobilis and *Saccharomyces* sp. Appl Microbiol Biotechnol., 1996, vol. 45: 580-583. (Year: 1996).*
Agrawal et al., Fermentation of Paddy Malt Mash to Ethanol by Mixed Cultures of *Saccharomyces* cerevisiae and Zymomonas mobilis ZM4 with Penicillin G. J. Ferment. Bioengg., 1994, vol. 77(2): 218-220. (Year: 1994).*
Amin et al., Determination of By-Products Formed During the Ethanolic Fermentation, Using Batch and Immobilized Cell Systems of Zymomonas mobilis and *Saccharomyces* bayanus. Eur J Appl Microbiol Biotechnol., 1983, vol. 18: 1-5. (Year: 1983).*
Chen (2011) "Development and application of co-culture for ethanol production by co-fermentation of glucose and xylose: a systematic review" Journal of Industrial Microbiology & Biotechnology 38:581-597.
Davidson and Stephanopoulos (1986) "Effect of pH oscillations on a competing mixed culture" Biotechnology and Bioengineering 28(8):1127-1137.
Faria-Oliveira et al. (2015) "The role of yeast and lactic acid bacteria in the production of fermented beverages in South America".
Finn (2014) "Understanding bacterial adaptation to aerobic and anaerobic environments through experimental evolution and whole genome analysis : a thesis presented in fulfilment of the requirements for the degree of Doctor of Philosophy in Genetics at Massey University, Palmerston North, New Zealand".
Goers et al. (2014) "Co-culture systems and technologies taking synthetic biology to the next level" Journal of the Royal Society 11:20140065.
Hanly and Henson (2013) "Dynamic metabolic modeling of a microaerobic yeast co-culture: predicting and optimizing ethanol production from glucose/xylose mixtures" Biotechnology for Biofuels 6:44.
Kato et al. (1997) "Anaerobe tolerance to oxygen and the potentials of anaerobic and aerobic cocultures for wastewater treatment" Braz. J. Chem. Eng. 14(4):.
Park et al. (2012) "One-pot bioethanol production from cellulose by co-culture of Acremonium cellulolyticus and *Saccharomyces* cerevisiae" Biotechnology for Biofuels 5:64.
Stephens and Lyberatos (1987) "Effect of cycling on final mixed culture fate" Biotechnology and Bioengineering 29(6):672-678.
Zuroff et al. (2013) "Consortia-mediated bioprocessing of cellulose to ethanol with a symbiotic Clostridium phytofermentans/yeast co-culture" Biotechnology for Biofuels 6: 59.
Moscoviz et al. (2021) "Directing carbohydrates toward ethanol using mesophilic microbial communities" Current Opinion in Biotechnology 67:175-183.

* cited by examiner

*Primary Examiner* — Ganapathirama Raghu
(74) *Attorney, Agent, or Firm* — FisherBroyles, LLP; Cara L. Crowley-Weber; Cary Reeves

(57) ABSTRACT

Methods, compositions, and systems for propagation and fermentation, particularly large scale operations for production of ethanol and dried distiller's grain are provided. Addition of Z. mobilis to propagation and/or fermentation decreases lactic acid bacterial contamination.

14 Claims, 10 Drawing Sheets

SYSTEMS, COMPOSITIONS, AND METHODS OF FERMENTATION WITH *Z. MOBILIS*

RELATED APPLICATIONS

This application claims the benefit of U.S. Provisional Application No. 62/988,050 titled "Systems, Compositions, and Methods of Fermentation with *Z. mobilis*" filed Mar. 11, 2020, which are incorporated herein by reference.

TECHNICAL FIELD

Provided herein are methods, compositions, and systems for propagation and fermentation, particularly in large scale operations for production of ethanol and dried distiller's grain.

BACKGROUND

The gram negative facultative anaerobic bacterium, *Zymomonas mobilis* (*Z. mobilis*) has been considered as a potential alternative to yeast for ethanol production. The use of *Z. mobilis* has advantages over yeast, including higher specific rate of sugar uptake, lower biomass production, and higher volumetric sugar uptake and ethanol productivity. A commonly known drawback of *Z. mobilis* is that it can tolerate only up to approximately 12 percent weight to volume ethanol (approximately 15.2 percent volume to volume) whereas yeast can tolerate up to approximately 18 percent weight to volume (approximately 23 percent volume to volume).

In a conventional raw starch hydrolysis process, where very high gravity (VHG) fermentation is practiced, a commercially available distiller's yeast is able to produce approximately 15 to 16 percent weight to volume ethanol (approximately 19 to 20.2 percent volume to volume ethanol). In the raw starch hydrolysis process, which has no cooking (liquefaction) step a higher probability exists that the mash may become contaminated by bacteria that produce undesirable end-products.

One substantial source for contaminant bacteria in an ethanol production facility is the feedstock. As much as 10,000 to 1,000,000 bacterial cells per gram enter the facility with the incoming corn. A majority of contaminant bacteria belong to the lactic acid bacterial group since they can adapt and grow well in the ethanol production conditions. Eventually, these contaminant lactic bacteria get established in the production facility if proper measures for control are not taken.

A number of strategies, including the use of low pH (between pH of 4.2 to 4.5) in fermentation, minimal use of antibiotics, and good plant management practices are used to keep the levels of contaminant bacteria to a small quantity. However, natural "non-antibiotic" solutions that eliminate the effects caused by these contaminant bacteria are desirable.

Running antibiotic-free industrial ethanol fermentations is desirable in consideration of global issues surrounding development of antibiotic resistant bacteria.

Wild lactic acid bacteria have a faster growth rate than yeast under ideal conditions. These bacteria, when they are in high numbers in the substrate, can begin to grow rapidly even before yeast is inoculated (added) to the mash. The lactic acid bacteria can easily grow to levels that would produce enough end-products, including lactic and acetic acids, to slow down the efficiency of ethanol production by the yeast, ultimately leading to a loss in ethanol yield.

The present disclosure is directed toward overcoming one or more of the problems discussed above.

SUMMARY

Provided herein are compositions, methods, and systems for propagation and fermentation, for example, fermentation used in the production of bioethanol.

Provided herein are compositions comprising a primary feedstock, a yeast such as *S. cerevisiae*, *Z. mobilis*, and water. The primary feedstock comprises the sugar source for propagation and fermentation by the microorganisms.

Also provided herein are compositions comprising a primary feedstock, a yeast such as *S. cerevisiae*, *Z. mobilis*, hop acids, and water. In some aspects, the hop acids are present in the composition in an amount of about 25 ppm to about 40 ppm.

Provided herein are methods of reducing contamination during ethanol production in the raw starch hydrolysis process by utilizing *Z. mobilis* as a "probiotic" inoculant to combat lactic acid bacterial infection and contamination. The methods comprise (a) combining a feedstock, a yeast, *Z. mobilis*, and water in a propagator and/or fermenter; and (b) fermenting the feedstock.

Provided herein are methods of reducing undesired bacterial contamination, such as lactic acid bacterial contamination, in a fermentation. In some aspects, the method comprises adding *Z. mobilis* to a raw starch hydrolysis reaction.

Provided herein are methods of ethanol fermentation. In some embodiments, the method comprises (a) inoculating a feedstock with *S. cerevisiae* and *Z. mobilis*, and (b) fermenting the feedstock to produce ethanol. In some aspects, the feedstock is inoculated with *Z. mobilis* prior to or during *S. cerevisiae* propagation. In some aspects, the feedstock is inoculated with *Z. mobilis* prior to or during fermentation. Fermentations carried out with a yeast and *Z. mobilis* co-culture can exhibit decreased levels of lactic acid bacteria by at least about 5% relative to a fermentation in the absence of *Z. mobilis*. Fermentations carried out with a yeast and *Z. mobilis* co-culture result in little or no fusel oils in the fermentation solids that may be subsequently separated from stillage and dried to form DDG. Fermentations carried out with a yeast and *Z. mobilis* co-culture can exhibit decreased glycerol content in the fermentation solids relative to a fermentation in the absence of *Z. mobilis*. In some aspects, ethanol yield is increased relative to a fermentation in the absence of *Z. mobilis*. In some aspects, yeast numbers are decreased after fermentation relative to a fermentation in the absence of *Z. mobilis*.

*Z. mobilis* has a faster growth rate compared to yeast and lactic acid bacteria and, therefore, when inoculated at sufficient levels, is better able than yeast to compete with contaminant lactic bacteria. *Z. mobilis* can produce ethanol in a mixed culture with yeast cells in a high solids environment, and the present disclosure utilizes *Z. mobilis* as a "probiotic" to combat lactic bacterial infection during ethanol production by *Saccharomyces cerevisiae* (*S. cerevisiae*).

During the production of ethanol by yeast, some of the fermentable substrate is diverted to the production of by-products such as glycerol, amyl alcohol and other fusel oils. Ethanol produced from molasses fermentation by a mixture of *Z. mobilis* and yeast contained little or no fusel oils. *Z. mobilis* has an extremely efficient carbohydrate to ethanol process via the Entner-Doudoroff pathway. This metabolic pathway catabolizes glucose to pyruvate using different enzymes from those used in glycolysis or the pentose phosphate pathway.

In some embodiments provided herein, glycerol content of fermentation solids is reduced providing benefits in the downstream processing and flowability of dried distiller's grains.

In some embodiments provided herein, Z. mobilis crowds out the contaminant lactic acid bacteria because of its faster growth rate.

In some embodiments provided herein, the addition of Z. mobilis to the fermentation, either through introduction in propagation or direct introduction into early fermentation also increases ethanol yield, especially in shorter hour fermentations.

In some embodiments provided herein, Z. mobilis also improves antibiotic free fermentations due to its tolerance to hop acids, a non-antibiotic antimicrobial agent. Provided herein are methods of antibiotic free fermentation. In some aspects, the methods comprise (a) inoculating a feedstock with S. cerevisiae and Z. mobilis; (b) adding hop acids, and (c) fermenting the feedstock.

In some embodiments, provided herein are compositions comprising dried distiller's grain (DDG) with antibacterial activity. The DDG can exhibit antibacterial activity, among other unexpected characteristics because Z. mobilis produces microbial levan which can have antibacterial and antifungal activity. The antibacterial activity of the DDG is relative to the lack of antibacterial activity exhibited by DDG obtained from fermentation performed in the absence of Z. mobilis.

DESCRIPTION

Figure 1:
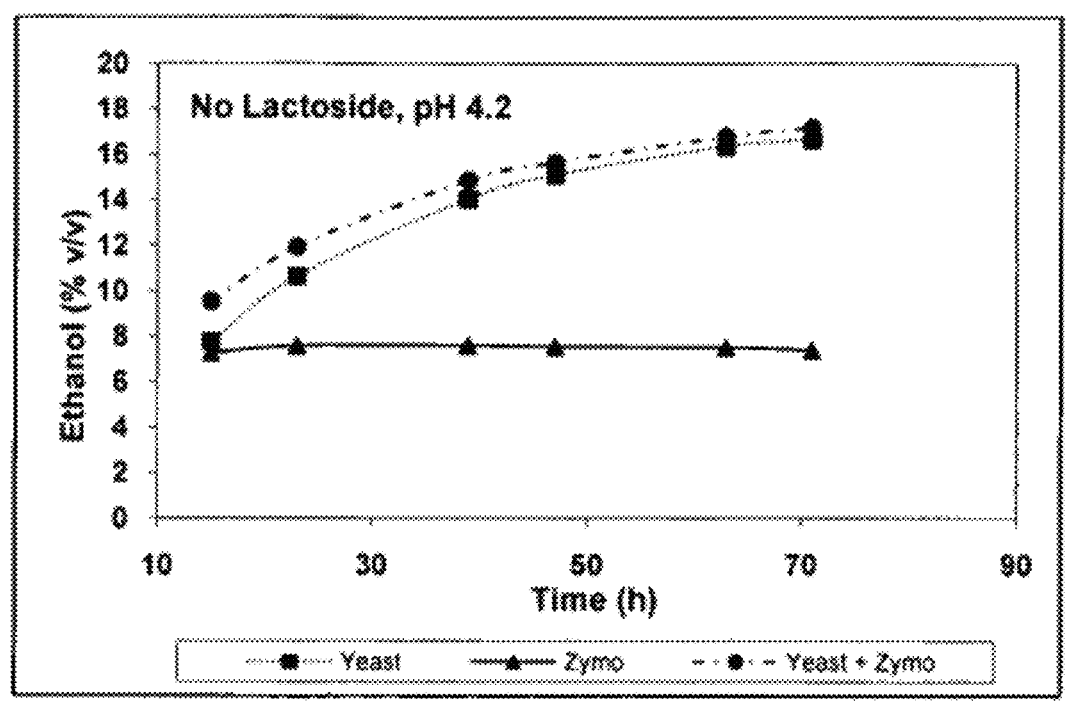
FIG. 1, FIG. 2, FIG. 3, and FIG. 4 illustrate ethanol production kinetics at varying pHs and with and without lactoside.
Figure 2:
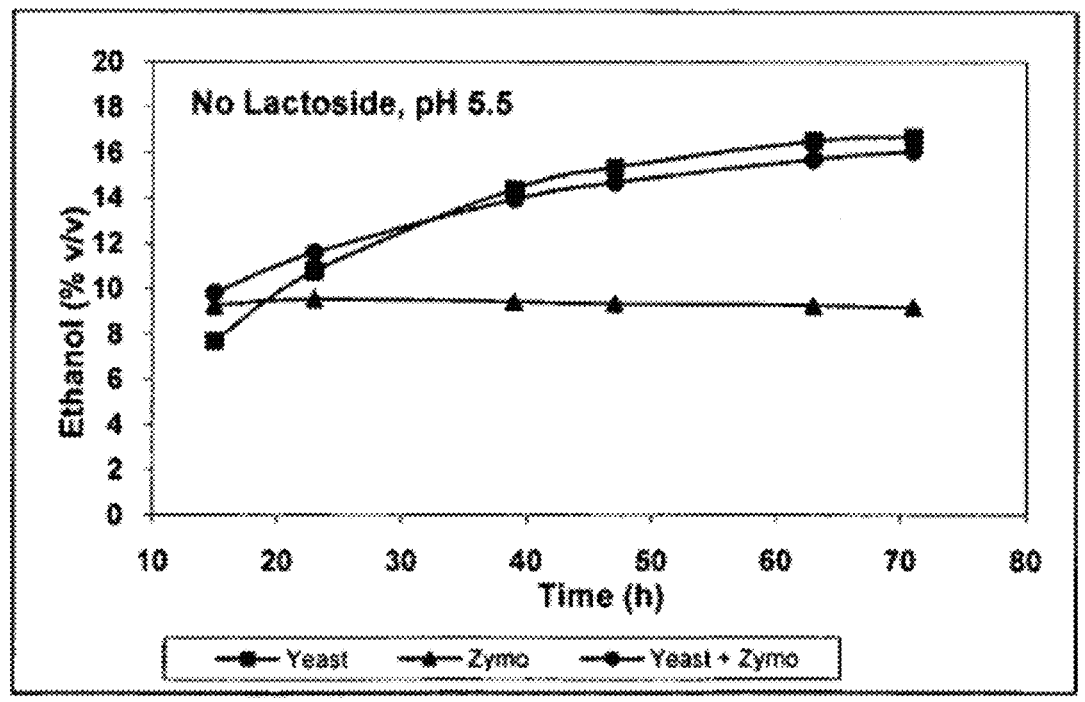
Figure 3:
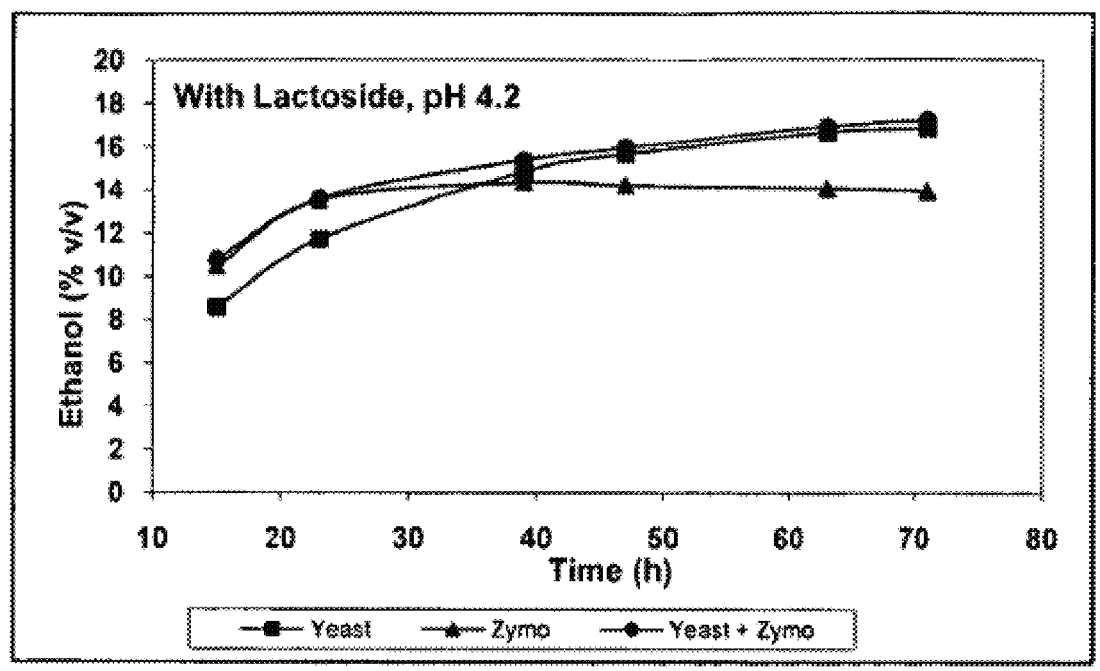
Figure 4:
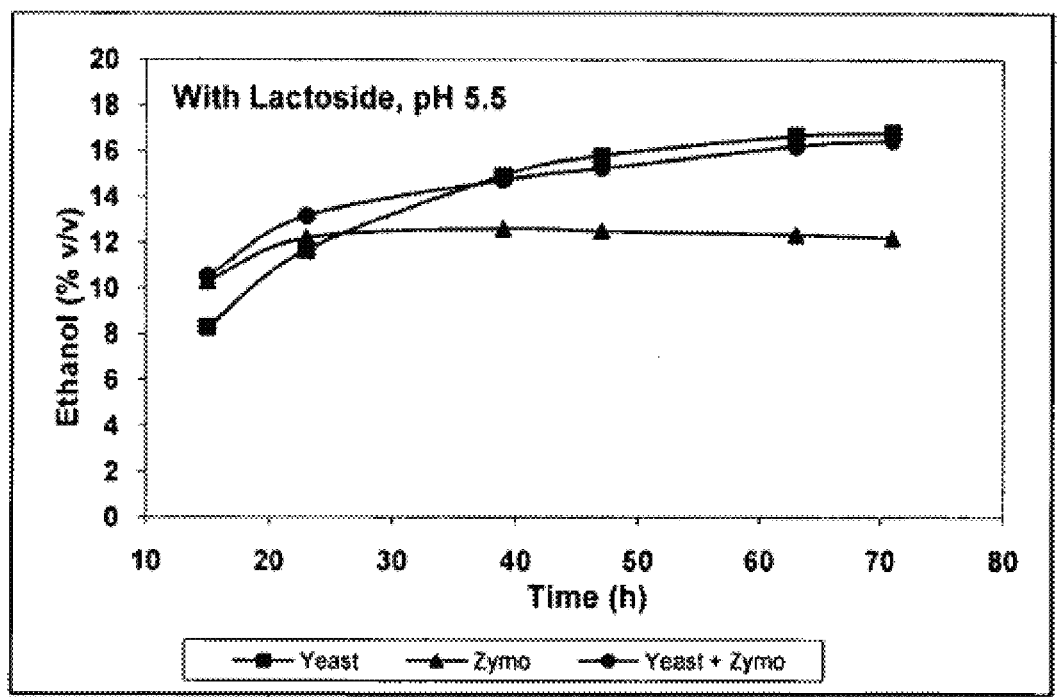

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All patents, applications and non-patent publications mentioned in this specification are incorporated herein by reference in their entireties.

Industrial fermentation involves the breakdown of a feedstock by one or more microorganisms, e.g. yeast and/or bacteria, into one or more products. In addition to the feedstock, other nutrients may be provided to the organism to facilitate the fermentation. For example, a traditional ethanol fermentation process utilizes grain-based feedstocks (e.g., corn, sorghum/milo, barley, wheat, etc.), or other sugar sources (e.g., sugar cane, sugar beets, etc.). Enzymes, whether endogenous to the grain, added to the fermenter, or produced by yeast, convert components of the feedstock into simple sugars. Yeast, acting subsequent to or simultaneously with the enzymes, convert the simple sugars to ethanol and carbon dioxide.

In a typical ethanol production plant, corn, or other suitable primary feedstock is ground for fermentation. The entire corn kernel can be ground for fermentation, or the corn kernel may be fractionated into its component parts, and only the starchy endosperm ground for use in fermentation. Any suitable feedstock, subjected to virtually any suitable pretreatment, can be used in the methods and compositions provided herein.

The ground corn or other primary feedstock may be combined with water to form a slurry, and the pH of the slurry mixture may be adjusted as needed. A microorganism, for example, a yeast such as S. cerevisiae, is added. The amount of yeast starter employed is selected to effectively produce a commercially significant quantity of ethanol in a suitable time, e.g., less than 75 hours or less than 88 hours.

Yeast can be added to the fermentation by any of a variety of methods known for adding yeast to fermentation processes. Other desired components can be added to the fermenter, including certain enzymes which produce monomeric sugars from polymeric sugars (e.g. glucose from starch) in the fermentable solids as in simultaneous saccharification and fermentation (SSF). These enzymes can be commercially sourced, may be present in the feedstock (genetically modified corn, for example), or may be expressed by the yeast. Exemplary enzymes include glucoamylase and alpha-amylase. Alternatively, saccharification can be performed separate from fermentation.

The slurry can be held at specified temperatures to facilitate the production of ethanol for a determined period of time. Fermenting can include contacting a mixture including sugars from the reduced plant material (e.g., fractionated plant material) with yeast under conditions suitable for growth of the yeast and production of ethanol. During fermentation, the yeast converts the sugars (e.g. glucose) to ethanol and carbon dioxide, and between the enzymatic production of sugars (e.g. glucose) and the fermentation process, sugars (e.g. glucose) may be maintained in the system at a low steady state. After fermentation, further treatment and/or distillation is performed to recover the ethanol, oil, carbon dioxide, dried distiller's grains (DDG), and/or other co-products.

It has been determined and disclosed herein that addition of Z. mobilis to propagation and/or fermentation can be beneficial to ethanol production. As such, provided herein are compositions, methods, and systems for propagation and fermentation utilizing Z. mobilis with a yeast such as S. cerevisiae.

In the conventional raw starch hydrolysis process, approximately 15 to 16 percent ethanol by weight (19 to 20.2 percent volume to volume) is produced using the yeast, S. cerevisiae. In some aspects, a co-culture of both Z. mobilis and S. cerevisiae can reduce glycerol production. In some aspects, including Z. mobilis in a co-culture with S. cerevisiae does not negatively impact ethanol production, and in some aspects, can increase ethanol production.

In an exemplary embodiment, utilization of a co-culture is advantageous because Z. mobilis helps consume any glucose spike that might occur and its fast growth and alcohol production can suppress lactic acid bacteria contamination early in propagation or fermentation while the yeast can continue producing ethanol after the ethanol concentration has become inhibitory to the Z. mobilis.

This co-culture addresses and resolves the initial glucose spike that is generally observed in the fermentation process due to enzymes (as Z. mobilis is known to tolerate higher glucose levels). Since Z. mobilis uses a different pathway to produce ethanol, glycerol production is less. Glycerol production by the coculture is reduced compared to yeast only culture because the consumption of a portion of the glucose by Z. mobilis prevents its conversion to glycerol by yeast and because consumption of a portion of the glucose by Z. mobilis reduces any glucose stress on the yeast so that the less stressed yeast produces less glycerol. The reduction in glycerol production is an additional benefit of the present disclosure. Reduced glycerol provides downstream processing benefits as well as improvement in coproduct quality.

Yeasts useful according to the embodiments described herein are any yeasts typically useful in converting feedstock into ethanol, especially in an industrial setting. Such yeasts may include, e.g., various strains of Saccharomyces cerevisiae such as, non-genetically modified commodity yeasts; consolidated bioprocessing yeasts (CBP, expressing glucoamylase and/or alpha-amylase); yeast genetically modified for various purposes; a genetically modified yeast blend; and a genetically modified thermotolerant yeast.

Compositions

The disclosure encompasses compositions comprising a primary feedstock, Z. mobilis, a yeast, and water. Such compositions can further comprise one or more of hop acids, a cellulase, xylanase, lipase, protease, and phytase.

The yeast can be genetically modified or non-GMO.

The disclosure also encompasses compositions comprising DDG. The DDG can exhibit antibacterial activity, among other unexpected characteristics. Z. mobilis produces microbial levan which can have antibacterial and antifungal activity. The improved DDG are relative to the DDG obtained from fermentation performed in the absence of Z. mobilis.

Systems

Further provided herein are systems in which the methods and/or compositions disclosed herein are useful. In some aspects, a fermenter or propagator contains a composition as described above, e.g. a feedstock, a yeast, Z. mobilis, and water. The fermenter or propagator can further contain at least one enzyme, at least one priming agent, and/or a pH adjusting agent.

In some aspects, the at least one priming agent is a weak acid such as acetic acid at low levels.

Further provided are systems for ethanol production comprising one or more fermenters containing the compositions described herein. In some aspects, the system further comprises at least one of the following: a mill for preparation of feedstock; a propagator; and a distillation system.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided for illustrative purposes only and are not intended to limit the scope of the invention.

Example 1: Co-Culture of Zymomonas and S. cerevisiae

Yeast only, Z. mobilis only, and a coculture of yeast and Z. mobilis were compared at varying pH and with and without Lactoside. L. plantarum was included to simulate lactic acid bacteria contamination.

Preparation of Mash

In an embodiment provided herein, ground corn was mixed with "preblend" (a mixture of the waters from various streams that are reused in an ethanol production facility, e.g. thin stillage) in an appropriate ratio to obtain slurry (mash) with 35 percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8. Depending on the required pH for the study, pH was adjusted using either 10 percent volume to volume sulfuric acid or using 45 percent weight to weight potassium hydroxide. An enzyme blend for raw starch hydrolysis was added to the slurry. The enzyme blend was added to target a dose of 0.0475-0.065 FAU-F/g DS (acid fungal amylase) and 0.4-0.5 AGUs/g DS (amyloglucosidase). Urea (32 percent liquor) was added to the slurry to give a final concentration of approximately 1 mM urea. The slurry was mixed and dispensed into 125 milliliter Erlenmeyer flasks at 70 milliliters per flask.

Preparation of Inoculum

Each flask containing mash was inoculated with yeast and/or Z. mobilis as indicated in Table 1. In addition, each flask was inoculated with L. plantarum to represent a contaminating bacteria.

The ATCC31821 culture (*Z. mobilis* (ATCC #31821)) was grown in Zymo-MRM 1 medium (a growth medium containing 50 grams/Liter Glucose, 10 grams/Liter Yeast extract, 2 grams/Liter KH2PO4, 1 grams/Liter Ammonium sulfate, and magnesium sulfate) at 30 degrees Celsius overnight (approximately 17 h) and then this culture was re-inoculated into fresh Sterile Zymo-MRM 1 medium at 5 milliliter in 50 milliliter and grown for 8 hours at 30 degrees Celsius. This 8 hour culture was used as the inoculum for the mash at 10.0 percent inoculation level. An amount of the culture was harvested and resuspended to 2 milliliters in sterile deionized water. The culture was then used to inoculate the mash.

*Lactobacillus plantarum* was used as the inoculum for the mash at approximately 1e07 cells per milliliter. The culture was grown exactly the same as *Z. mobilis* but in MRS broth (a growth medium containing polysorbate, acetate, magnesium and manganese). About 0.70 milliliter of an 8 hour old culture in MRS broth when inoculated to 70 milliliter reactor produced approximately 1e07-1e08 cells per milliliter.

*Saccharomyces cerevisiae*, (Ethanol red) active dry yeast was rehydrated in sterile deionized water for approximately 20 minutes prior to inoculation of the mash. Appropriate quantities of this suspension were added to the mash to obtain an inoculation level of approximately 1e07 cells per milliliter.

Fermentation

The flasks were covered with double layered aluminum foil after inoculation of the necessary organisms and placed in a water bath shaker (175 rpm). The fermentation temperature was staged: 32.2 degrees Celsius for 0 to 24 hours; 28.9 degrees Celsius for 24 to 48 hours; and 27.8 degrees Celsius for 48 hours until the end. Samples were withdrawn at various intervals during the course of fermentation and analyzed for sugars, organic acids and ethanol using high performance liquid chromatography (HPLC) with a Aminex HPX-87H column, commercially available from Bio-Rad Laboratories, Hercules, Calif.

Table 1 shows that *Zymomonas* can be successfully grown in co-culture with the yeast. FIGS. 1 through 4 illustrate ethanol production kinetics at varying pH and with and without lactoside. Lactoside is an antimicrobial that can be used in fermentations and contains one or more antibiotics to reduce fermentation contamination from bacteria such as *Lactobacillus, Acetobacter, Leuconostoc,* and *Pediococcus*.

TABLE 1

Fermentation Results of Co-Culture

| | | | EtOH % v/v | DP4+ % w/v | DP3 % w/v | Malt % w/v | Gluc % w/v | Fruc % w/v | Lactic ppm | Glyc % w/v | Acetic ppm | Starch % dw | Prot % dw |
|---|---|---|---|---|---|---|---|---|---|---|---|---|---|
| With Lactoside247 | pH 4.5 | Yeast | 12.56 | 0.62 | 0.08 | 0.08 | 0.21 | 0.26 | 639 | 1.04 | 176 | ND | ND |
| | | Zymo | 12.79 | 0.62 | 0.09 | 0.06 | 0.24 | 0.15 | 390 | 0.44 | 627 | ND | ND |
| | | Y + Z | 13.19 | 0.62 | 0.09 | 0.07 | 0.20 | 0.18 | 403 | 0.76 | 329 | ND | ND |
| | pH 5.8 | Yeast | 12.24 | 0.57 | 0.09 | 0.08 | 0.34 | 0.31 | 619 | 1.11 | 234 | ND | ND |
| | | Zymo | 11.68 | 0.57 | 0.09 | 0.05 | 0.16 | 0.15 | 550 | 0.42 | 846 | ND | ND |
| | | Y + Z | 13.20 | 0.55 | 0.09 | 0.05 | 0.23 | 0.16 | 375 | 0.70 | 612 | ND | ND |
| 24 Hour Fermentation Results - Average of Duplicates | | | | | | | | | | | | | | |
| No Lactoside247 | pH 4.5 | Yeast | 12.44 | 0.60 | 0.09 | 0.07 | 0.21 | 0.26 | 603 | 1.04 | 176 | ND | ND |
| | | Zymo | 12.52 | 0.60 | 0.09 | 0.06 | 0.21 | 0.15 | 436 | 0.43 | 596 | ND | ND |
| | | Y + Z | 13.07 | 0.60 | 0.09 | 0.06 | 0.22 | 0.18 | 440 | 0.78 | 282 | ND | ND |
| | pH 5.8 | Yeast | 11.91 | 0.56 | 0.09 | 0.07 | 0.31 | 0.29 | 709 | 1.11 | 203 | ND | ND |
| | | Zymo | 11.32 | 0.55 | 0.09 | 0.05 | 0.17 | 0.14 | 760 | 0.42 | 856 | ND | ND |
| | | Y + Z | 12.94 | 0.54 | 0.09 | 0.05 | 0.22 | 0.16 | 433 | 0.70 | 555 | ND | ND |
| With Lactoside247 | pH 4.5 | Yeast | 16.54 | 0.57 | 0.07 | 0.04 | 0.06 | 0.24 | 318 | 1.07 | 438 | ND | ND |
| | | Zymo | 14.91 | 0.61 | 0.08 | 0.11 | 1.24 | 0.12 | 67 | 0.48 | 773 | ND | ND |
| | | Y + Z | 16.27 | 0.58 | 0.08 | 0.05 | 0.09 | 0.14 | 191 | 0.77 | 634 | ND | ND |
| | pH 5.8 | Yeast | 16.73 | 0.53 | 0.08 | 0.05 | 0.08 | 0.24 | 313 | 1.14 | 714 | ND | ND |
| | | Zymo | 15.96 | 0.51 | 0.08 | 0.03 | 0.36 | 0.05 | 103 | 0.43 | 1235 | ND | ND |
| | | Y + Z | 17.04 | 0.52 | 0.08 | 0.04 | 0.12 | 0.13 | 205 | 0.71 | 1071 | ND | ND |
| 48 Hour Fermentation Results - Average of Duplicates | | | | | | | | | | | | | | |
| No Lactoside247 | pH 4.5 | Yeast | 16.43 | 0.57 | 0.08 | 0.04 | 0.06 | 0.22 | 259 | 1.06 | 486 | ND | ND |
| | | Zymo | 15.06 | 0.60 | 0.08 | 0.09 | 1.19 | 0.12 | 131 | 0.48 | 792 | ND | ND |
| | | Y + Z | 16.33 | 0.57 | 0.08 | 0.05 | 0.09 | 0.14 | 230 | 0.80 | 572 | ND | ND |
| | pH 5.8 | Yeast | 16.43 | 0.53 | 0.08 | 0.04 | 0.07 | 0.22 | 457 | 1.17 | 581 | ND | ND |
| | | Zymo | 15.70 | 0.50 | 0.08 | 0.02 | 0.30 | 0.14 | 256 | 0.43 | 1403 | ND | ND |
| | | Y + Z | 16.72 | 0.51 | 0.08 | 0.04 | 0.11 | 0.13 | 217 | 0.72 | 1079 | ND | ND |
| With Lactoside247 | pH 4.5 | Yeast | 17.80 | 0.56 | 0.07 | 0.04 | 0.03 | 0.22 | 141 | 1.08 | 639 | 9.11 | 27.42 |
| | | Zymo | 14.54 | 0.61 | 0.08 | 0.13 | 2.69 | 0.14 | 54 | 0.48 | 771 | 26.35 | 20.17 |
| | | Y + Z | 17.57 | 0.56 | 0.08 | 0.04 | 0.06 | 0.13 | 82 | 0.79 | 814 | 12.50 | 26.27 |
| | pH 5.8 | Yeast | 17.98 | 0.52 | 0.08 | 0.04 | 0.03 | 0.22 | 145 | 1.15 | 909 | 8.69 | 27.72 |
| | | Zymo | 15.69 | 0.53 | 0.08 | 0.06 | 2.21 | 0.11 | 101 | 0.43 | 1226 | 22.73 | 21.95 |
| | | Y + Z | 18.16 | 0.50 | 0.08 | 0.04 | 0.08 | 0.14 | 108 | 0.73 | 1253 | 11.13 | 26.77 |
| 71 Hour Fermentation Results - Average of Duplicates | | | | | | | | | | | | | | |
| No Lactoside247 | pH 4.5 | Yeast | 17.74 | 0.55 | 0.08 | 0.03 | 0.03 | 0.21 | 102 | 1.06 | 662 | 8.85 | 27.39 |
| | | Zymo | 14.29 | 0.60 | 0.08 | 0.12 | 2.53 | 0.12 | 159 | 0.48 | 766 | 26.25 | 20.02 |
| | | Y + Z | 17.63 | 0.56 | 0.08 | 0.04 | 0.05 | 0.14 | 103 | 0.81 | 715 | 13.55 | 27.7 |
| | pH 5.8 | Yeast | 17.86 | 0.51 | 0.08 | 0.03 | 0.03 | 0.21 | 231 | 1.18 | 740 | 9.27 | 28.25 |
| | | Zymo | 15.62 | 0.52 | 0.08 | 0.05 | 2.03 | 0.00 | 118 | 0.42 | 1404 | 23.58 | 22.2 |
| | | Y + Z | 17.88 | 0.49 | 0.08 | 0.03 | 0.07 | 0.13 | 127 | 0.73 | 1307 | 11.39 | 27.33 |

Example 2: Inclusion of Z. mobilis in Fermentation

Yeast only (Novozymes Innova PT), Z. mobilis only, and a coculture of yeast and Z. mobilis were compared. No lactic acid bacteria were added but wild lactic acid bacteria were not excluded.

Preparation of Inoculum

Saccharomyces cerevisiae, as a commercial cream yeast, was added to a yeast propagation set up as follows. Ground corn was mixed with "preblend" (a mixture of the waters from various streams that are reused in an ethanol production facility) in an appropriate ratio to obtain slurry (mash) with 35 percent dry solids (including the solids contributed by the preblend water). "Preblend" was used as make up water in these studies to simulate the composition of mash, employing an exemplary embodiment, as it would be in a commercial ethanol production facility. The pH of the corn and "preblend" slurry was approximately 4.5-4.8. An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase). The dose was the same for all samples. Urea (50 percent liquor) was added to the slurry to give a final concentration of approximately 1000 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the yeast and placed stationary in a water bath. The fermentation temperature was held constant at 32.2 degrees Celsius for 8 hours. This yeast propagation was then used to inoculate the mash, for fermentations including yeast, at a ratio level of approximately 3 v/v % total fermentation volume. The amount was the same for all samples.

ATCC31821 culture (Z. mobilis (ATCC #31821)) was grown in 6% Zymo medium (a growth medium containing 60 grams/Liter Glucose, 10 grams/Liter Yeast extract, and 10 grams/Liter peptone) at 32.2 degrees Celsius overnight (approximately 18-24 h). This culture was concentrated to an OD600 of 20 in deionized water and used as the inoculum for the mash at a 1 v/v % inoculation level for samples containing Z. mobilis.

Preparation of Mash and Fermentation

Ground corn was mixed with "preblend" (a mixture of the waters from various streams that are reused in an ethanol production facility) in an appropriate ratio to obtain slurry (mash) with 34-38% percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8. An enzyme blend for raw starch hydrolysis was added to the slurry. The enzyme blend was added to target a dose of 0.005-0.05 FAU-F/g DS (acid fungal amylase) and 0.3-0.5 AGUs/g DS (amyloglucosidase). The dose was the same for all samples. Urea (50 percent liquor) was added to the slurry to give a final concentration of approximately 50-100 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 30.6 degrees Celsius for 88 hours. Bottles were mixed well and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Results

Figure 5:
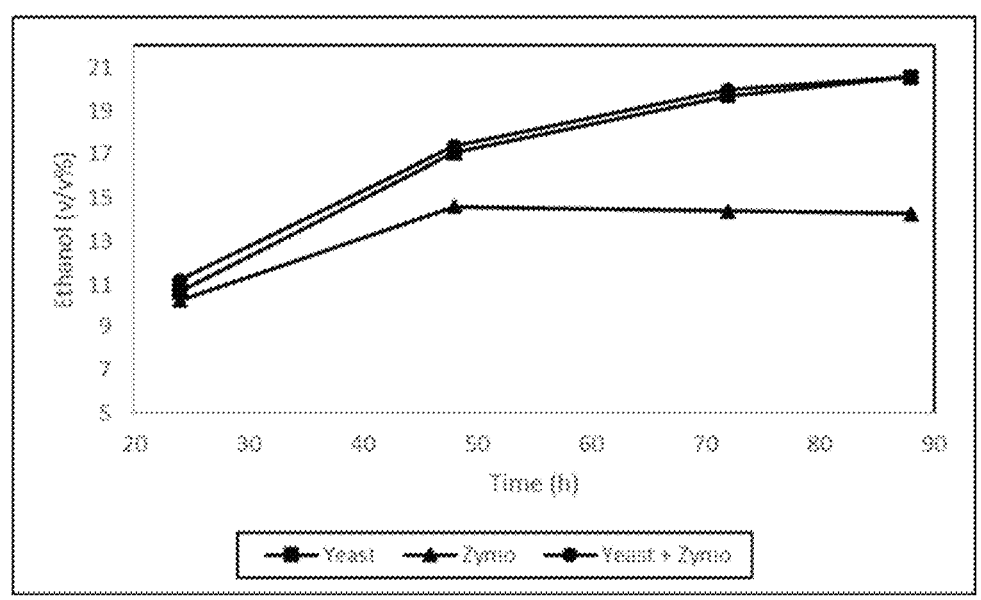
FIG. 5 illustrates ethanol levels produced during fermentation with Z. mobilis. Z. mobilis was added to fermenters during yeast propagation.

Table 2 and FIG. 5 show that at 88 hours, the coculture of yeast and Z. mobilis is able to make the same amount of ethanol from less starch than yeast alone as evidenced by higher residual starch levels in the resulting dry solids of the yeast and Z. mobilis coculture as compared to the yeast only culture. Glycerol levels are also 19.6% lower in fermentations containing both organisms. Lactic acid levels are approximately 8% lower in the fermentations including both organisms, indicating naturally improved contamination control. Higher acetic levels are noted due to acetic acid production by the Z. mobilis culture. FIG. 5 also illustrates that inclusion of Z. mobilis in fermentation does not negatively impact ethanol production.

TABLE 2

Analyte levels at 88 hours of fermentation

| | ETOH (v/v %) | DP4+ (w/v %) | DP3 (w/v %) | Malt (w/v %) | Gluc (w/v %) | Succ (w/v %) | Lactic (ppm) | Glyc (w/v %) | Acetic (ppm) | Starch (%) |
|---|---|---|---|---|---|---|---|---|---|---|
| Yeast | 20.57 | 0.36 | 0.04 | 0.01 | 0.06 | 0.16 | 2021 | 1.07 | 524 | 7.43 |
| Zymo | 14.27 | 0.43 | 0.03 | 0.11 | 6.54 | 0.13 | 2015 | 0.51 | 1483 | 23.85 |
| Yeast + Zymo | 20.57 | 0.39 | 0.03 | 0.02 | 0.34 | 0.18 | 1852 | 0.86 | 765 | 9.21 |

Example 3: Natural Priming and Reduction of Cell Number Through Z. mobilis Inclusion A yeast only control (Novozymes Innova PT) was compared to yeast and Z. mobilis cocultures of varying concentration. No lactic acid bacteria were added but wild lactic acid bacteria were not excluded.

Preparation of Inoculum

Saccharomyces cerevisiae, as a commercial cream yeast, was added to a yeast propagation set up as follows. Ground corn was mixed with "preblend" (a mixture of the waters from various streams that are reused in an ethanol production facility) in an appropriate ratio to obtain slurry (mash) with 35 percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8. An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase). The dose was the same for all samples. Urea (50 percent liquor)

was added to the slurry to give a final concentration of approximately 1000 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 32.2 degrees Celsius for 8 hours. This yeast propagation was then used to inoculate fermentations including yeast at a ratio level of 3-4% total fermentation volume.

ATCC31821 culture (Z. mobilis (ATCC #31821)) was grown in 6% Zymo medium (a growth medium containing 60 grams/Liter Glucose, 10 grams/Liter Yeast extract, and 10 grams/Liter peptone) at 32.2 degrees Celsius overnight (approximately 18-24 h). This culture was concentrated in deionized water and the OD600 read. Z. mobilis was added to fermentation at a 1% inoculation level of an OD correlating to 5, 10, 15, 20, and 30 immediately following yeast propagation addition prior to starting the fermentation period for those containing Z. mobilis and yeast.

Preparation of Mash and Fermentation

Ground corn was mixed with "preblend" (a mixture of the waters from various streams that are reused in an ethanol production facility) in an appropriate ratio to obtain slurry (mash) with 34-38 percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8. An enzyme blend for raw starch hydrolysis was added to the slurry. The enzyme blend was added to target a dose of 0.005-0.05 FAU-F/g DS (acid fungal amylase) and 0.3-0.5 AGUs/g DS (amyloglucosidase). The dose was the same for all samples. Urea (50 percent liquor) was added to the slurry to give a final concentration of approximately 50-100 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 30.6 degrees Celsius for 88 hours. Bottles were mixed well, and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Cell counts were obtained using a Nexcelom Cellometer X2. The method used was the Cellometer ViaStain Yeast Live/Dead Viability Kit, Nexcelom Product #CSK-0102.

Results

Figure 6:
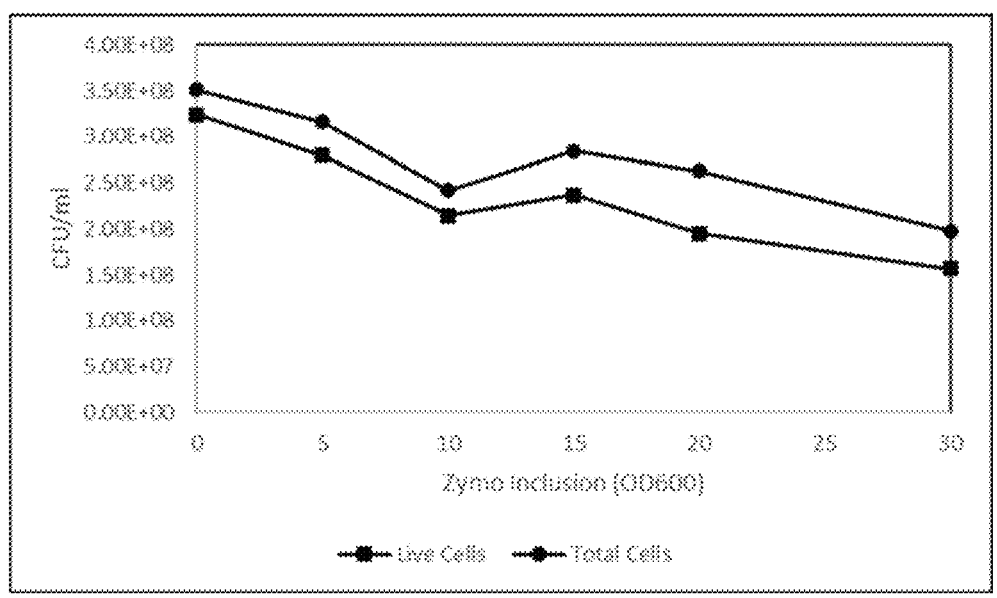
FIG. 6 illustrates the reduced live and total cell counts after fermentation with Z. mobilis. Z. mobilis was added to fermenters after yeast propagation.

Table 4 and FIG. 6 depicts cell counts at 24 hours. Z. mobilis was added at the beginning of fermentation (not propagation). Cell counts at 24 hours indicate that increased Z. mobilis inclusion in fermentation reduces both the live and total cell counts. Table 3 documents the analyte levels at 88 hours of fermentation. The acids produced by Z. mobilis reduce the yeast cell population which is termed cell priming. This contributes to the lower glycerol formation in the fermentation. Glycerol levels are lower in fermentations with Z. mobilis included. Similar ethanol levels were seen with more residual starch indicating a higher yield from the utilized starch. Increased acetic acid is also seen with increasing Z. mobilis inclusion.

TABLE 3 analyte levels at 88 hours of fermentation

| | ETOH (v/v %) | DP4+ (w/v %) | DP3 (w/v %) | Malt (w/v %) | Gluc (w/v %) | Succ (w/v %) | Lactic (ppm) | Glyc (w/v %) | Acetic (ppm) | Starch (%) |
|---|---|---|---|---|---|---|---|---|---|---|
| Yeast Only | 20.06 | 0.48 | 0.01 | 0.01 | 0.04 | 0.16 | 1635 | 1.08 | 589 | 10.42 |
| Zymo 5 | 20.12 | 0.50 | 0.01 | 0.01 | 0.12 | 0.15 | 1520 | 0.93 | 823 | 10.78 |
| Zymo 10 | 20.02 | 0.51 | 0.01 | 0.01 | 0.23 | 0.13 | 1587 | 0.85 | 869 | 12.11 |
| Zymo 15 | 19.90 | 0.53 | 0.01 | 0.02 | 0.35 | 0.12 | 1506 | 0.84 | 967 | 13.06 |
| Zymo 20 | 19.86 | 0.54 | 0.01 | 0.02 | 0.37 | 0.12 | 1500 | 0.84 | 1088 | 14.51 |
| Zymo 30 | 19.55 | 0.55 | 0.01 | 0.01 | 0.34 | 0.12 | 1490 | 0.83 | 1283 | 15.25 |

TABLE 4

24 hour cell counts

| Zymo Inclusion | Live | Total |
|---|---|---|
| 0 | 3.24E+08 | 3.51E+08 |
| 5 | 2.8E+08 | 3.16E+08 |
| 10 | 2.15E+08 | 2.42E+08 |
| 15 | 2.37E+08 | 2.85E+08 |
| 20 | 1.96E+08 | 2.63E+08 |
| 30 | 1.57E+08 | 1.98E+08 |

Example 4: Z. mobilis in Co-Propagation as an Alternative to Addition at Start of Fermentation Yeast only, Z. mobilis and yeast cofermentation in which Z. mobilis was added to fermentation, and Z. mobilis and yeast cofermentation in which Z. mobilis was added to propagation were compared.

Preparation of Inoculum

Saccharomyces cerevisiae, as a commercial cream yeast (Novozymes Innova PT), was added to a yeast propagation setup as follows. Ground corn was mixed with "preblend" (a mixture of the waters from various streams that are reused in an ethanol production facility) in an appropriate ratio to obtain slurry (mash) with 35 percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8. An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase). The dose was the same for all samples. Urea (50 percent liquor) was added to the slurry to give a final concentration of approximately 1000 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. ATCC31821 culture (Z. mobilis (ATCC #31821)) was grown in 6% Zymo medium (a growth medium containing 60 grams/Liter Glucose, 10 grams/Liter Yeast extract, and 10 grams/Liter peptone) at 32.2 degrees Celsius overnight (approximately 18-24 h). This culture was concentrated in deionized water and the OD600 read. This concentrate was used as the inoculum for the different copropagations at a 1% inoculation level of ODs correlating to 2.5, 5, 7.5, 10, 15, and 20. The Z. mobilis was added immediately following yeast addition in propagations containing both yeast and Z. mobilis. The propagation temperature was held constant at 32.2 degrees Celsius for 8 hours.

The propagations, with and without Z. mobilis, were then used to inoculate fermentations at a ratio level of approximately 3% v/v total fermentation volume to yield the samples indicated in Table 5. The samples includes a yeast only propagation and fermentation, a yeast only propagation with Zymomonas added to fermentation immediately prior to starting the fermentation period at a 1% inoculation level of an OD correlating to 10.

Preparation of Mash and Fermentation

In an embodiment provided herein, ground corn was mixed with "preblend" (a mixture of the waters from various streams that are reused in an ethanol production facility) in an appropriate ratio to obtain slurry (mash) with 34-38 percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8. An enzyme blend for raw starch hydrolysis was added to the slurry. The enzyme blend was added to target a dose of 0.005-0.05 FAU-F/g DS (acid fungal amylase) and 0.3-0.5 AGUs/g DS (amyloglucosidase). Urea (50 percent liquor) was added to the slurry to give a final concentration of approximately 50-100 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 30.6 degrees Celsius for 88 hours. Bottles were mixed well, and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Cell counts were obtained using a Nexcelom Cellometer X2. The method used was the Cellometer ViaStain Yeast Live/Dead Viability Kit, Nexcelom Product # CSK-0102.

Results

Figure 7:
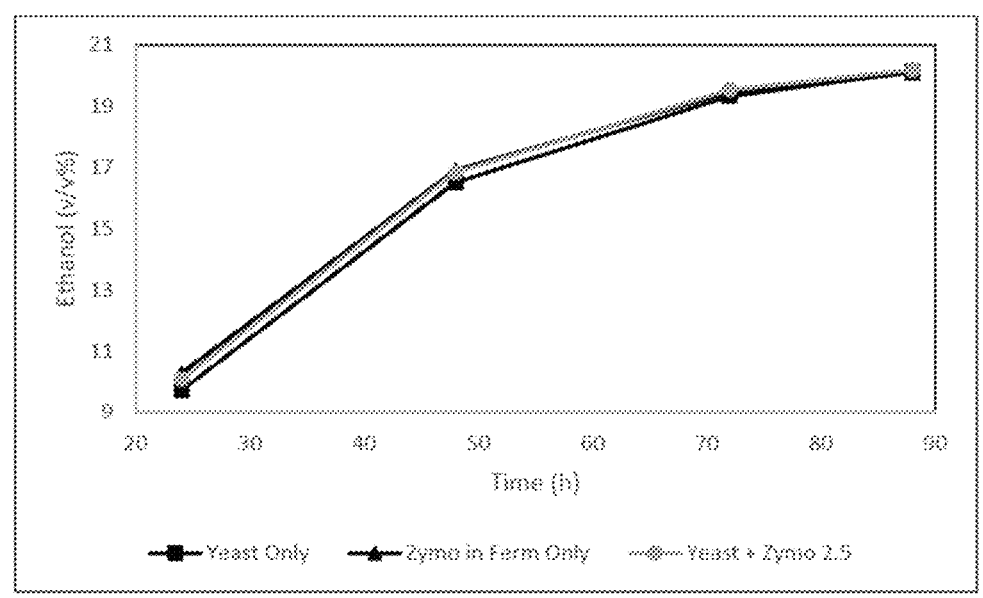
FIG. 7 illustrates that ethanol production in a fermentation performed after a yeast propagation with Z. mobilis is equal to or superior to ethanol production in cultures with either yeast alone or a fermentation where Z. mobilis is added at the start of fermentation rather than propagation.
Figure 8:
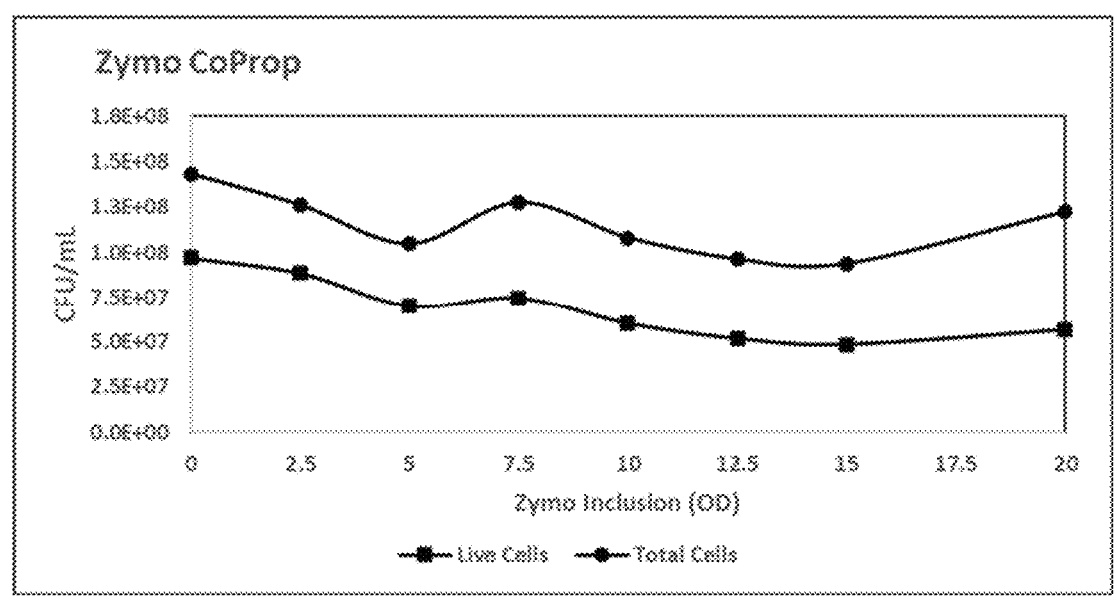
FIG. 8 illustrates the live and total yeast cells at the end of propagation with varying Z. mobilis inclusion levels.

Table 5 shows that at low levels of Z. mobilis inclusion into propagation (YP), the co-culture can perform equal to or superior to yeast alone or a fermentation with Z. mobilis added only at the start of fermentation. Glycerol levels are lower in all Z. mobilis containing fermentations, and lactic acid levels are also reduced. Increased acetic acid is seen when Z. mobilis inoculum is higher due to production of this byproduct by the Z. mobilis strain. FIG. 7 demonstrates that including Z. mobilis in the propagation media did not negatively impact ethanol production. FIG. 8 demonstrates decreased yeast cell counts at various levels of Z. mobilis in propagation medium.

TABLE 5

| Ferm | ETOH (v/v %) | DP4+ (w/v %) | DP3 (w/v %) | Malt (w/v %) | Gluc (w/v %) | Succ (w/v %) | Lactic (ppm) | Glyc (w/v %) | Acetic (ppm) | Starch (%) |
|---|---|---|---|---|---|---|---|---|---|---|
| fermentation products at 72 and 88 hours of fermentation ||||||||||| 
| 72 h ||||||||||| 
| Yeast only | 19.32 | 0.45 | 0.04 | 0.04 | 0.10 | 0.16 | 1616 | 1.05 | 518.41 | N.D. |
| Zymo in Ferm | 19.45 | 0.48 | 0.04 | 0.03 | 0.11 | 0.15 | 1481 | 0.89 | 692.72 | N.D. |
| YP 2.5 | 19.53 | 0.49 | 0.04 | 0.04 | 0.13 | 0.15 | 1516 | 0.91 | 665.93 | N.D. |
| YP 5 | 19.32 | 0.50 | 0.03 | 0.04 | 0.15 | 0.13 | 1485 | 0.85 | 811.57 | N.D. |
| YP 7.5 | 19.20 | 0.51 | 0.03 | 0.02 | 0.19 | 0.14 | 1495 | 0.84 | 875.20 | N.D. |
| YP 10 | 19.11 | 0.51 | 0.03 | 0.03 | 0.21 | 0.14 | 1467 | 0.82 | 944.91 | N.D. |
| YP 12.5 | 18.95 | 0.50 | 0.03 | 0.02 | 0.24 | 0.14 | 1479 | 0.82 | 1066.44 | N.D. |
| YP 15 | 18.78 | 0.51 | 0.03 | 0.02 | 0.27 | 0.14 | 1482 | 0.82 | 1036.33 | N.D. |
| YP 20 | 18.60 | 0.52 | 0.03 | 0.04 | 0.40 | 0.14 | 1513 | 0.83 | 1101.27 | N.D. |
| 88 h ||||||||||| 
| Yeast only | 20.13 | 0.44 | 0.04 | 0.04 | 0.06 | 0.19 | 1591 | 1.08 | 564.18 | 12.23 |
| Zymo in Ferm | 20.09 | 0.46 | 0.03 | 0.04 | 0.18 | 0.17 | 1482 | 0.91 | 748.69 | 11.38 |
| YP 2.5 | 20.18 | 0.48 | 0.04 | 0.04 | 0.22 | 0.17 | 1509 | 0.94 | 727.58 | 12.41 |
| YP 5 | 20.04 | 0.49 | 0.03 | 0.05 | 0.36 | 0.14 | 1489 | 0.88 | 864.66 | 13.00 |
| YP 7.5 | 19.89 | 0.49 | 0.04 | 0.05 | 0.45 | 0.15 | 1487 | 0.87 | 1004.37 | 14.59 |
| YP 10 | 19.94 | 0.49 | 0.04 | 0.06 | 0.57 | 0.15 | 1465 | 0.85 | 1014.08 | 14.87 |

TABLE 5-continued

| | fermentation products at 72 and 88 hours of fermentation | | | | | | | | |
|---|---|---|---|---|---|---|---|---|---|
| Ferm | ETOH (v/v %) | DP4+ (w/v %) | DP3 (w/v %) | Malt (w/v %) | Gluc (w/v %) | Succ (w/v %) | Lactic (ppm) | Glyc (w/v %) | Acetic (ppm) | Starch (%) |
| YP 12.5 | 19.86 | 0.49 | 0.04 | 0.06 | 0.52 | 0.15 | 1499 | 0.85 | 1064.84 | 15.84 |
| YP 15 | 19.79 | 0.50 | 0.04 | 0.06 | 0.50 | 0.15 | 1492 | 0.85 | 1068.89 | 16.90 |
| YP 20 | 19.79 | 0.52 | 0.04 | 0.07 | 0.62 | 0.15 | 1540 | 0.88 | 1168.46 | 17.65 |

TABLE 6 yeast cell counts at the end of propagation at varying Zymomonas inclusion levels

| | Live (CFU/mL) | Dead (CFU/mL) | Total (CFU/mL) | Viability (%) | Avg Size (um) |
|---|---|---|---|---|---|
| YP | 9.71E+07 | 4.64E+07 | 1.43E+08 | 67.7 | 5.8 |
| YP 2.5 | 8.86E+07 | 3.77E+07 | 1.26E+08 | 70.2 | 5.1 |
| YP 5 | 7.02E+07 | 3.46E+07 | 1.05E+08 | 67.0 | 5.4 |
| YP 7.5 | 7.46E+07 | 5.30E+07 | 1.28E+08 | 58.5 | 5.2 |
| YP 10 | 6.04E+07 | 4.77E+07 | 1.08E+08 | 55.8 | 4.8 |
| YP 12.5 | 5.18E+07 | 4.45E+07 | 9.63E+07 | 53.8 | 4.9 |
| YP 15 | 4.86E+07 | 4.53E+07 | 9.38E+07 | 51.8 | 5.2 |
| YP 20 | 5.68E+07 | 6.57E+07 | 1.22E+08 | 46.4 | 4.7 |

Example 5: Performance of Z. mobilis and Yeast in the Presence of Hop Acids for Antibiotic Free Fermentation Fermentations with yeast and various levels of hop acids and cofermentations of yeast and Z. mobilis with various levels of hop acids were conducted and compared to a yeast fermentation with lactoside.

Preparation of Inoculum

Saccharomyces cerevisiae, as a commercial cream yeast (Novozymes Innova PT), was added to a yeast propagation setup as follows. Ground corn was mixed with "preblend" (a mixture of the waters from various streams that are reused in an ethanol production facility) in an appropriate ratio to obtain slurry (mash) with 35 percent dry solids (including the solids contributed by the preblend water). "Preblend" was used as make up water in these studies to simulate the composition of mash, employing an exemplary embodiment provided herein, as it would be in a commercial ethanol production facility. The pH of the corn and "preblend" slurry was approximately 4.5-4.8. An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase). Urea (50 percent liquor) was added to the slurry to give a final concentration of approximately 1000 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the yeast and placed stationary in a water bath. The fermentation temperature was held constant at 32.2 degrees Celsius for 8 hours. This yeast propagation was then used to inoculate fermentations including yeast at a ratio level of 3-4% total fermentation volume.

ATCC31821 culture (Z. mobilis (ATCC #31821)) was grown in 6% Zymo medium (a growth medium containing 60 grams/Liter Glucose, 10 grams/Liter Yeast extract, and 10 grams/Liter peptone) at 32.2 degrees Celsius overnight (approximately 18-24 h). This culture was concentrated to an OD600 of 20 in deionized water and used as the inoculum for the mash at a 1% inoculation level into fermentation immediately following yeast propagation addition in cultures containing both yeast and Zymomonas, or immediately prior to starting the fermentation period for those containing only Zymomonas.

Preparation of Mash and Fermentation

Ground corn was mixed with "preblend" (a mixture of the waters from various streams that are reused in an ethanol production facility) in an appropriate ratio to obtain slurry (mash) with 34-38% percent dry solids (including the solids contributed by the preblend water). "Preblend" was used as make up water in these studies to simulate the composition of mash, as it would be in a commercial ethanol production facility. The pH of the corn and "preblend" slurry was approximately 4.8. An enzyme blend for raw starch hydrolysis was added to the slurry. The enzyme blend was added to target a dose of 0.005-0.05 FAU-F/g DS (acid fungal amylase) and 0.3-0.5 AGUs/g DS (amyloglucosidase). Urea (50 percent liquor) was added to the slurry to give a final concentration of approximately 50-100 ppm urea. The slurry was mixed in 100 milliliter wide mouth bottles at 60 milliliters per bottle. The bottles were covered with a bottle cap with a 1/16" hole drilled into the top for gas release following addition of enzyme, and inoculum, hop acids, and/or Lactoside as appropriate and placed stationary in a water bath. The fermentation temperature was held constant at 30.6 degrees Celsius for 88 hours. Bottles were mixed well, and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Hop acids were prepared at a 1:10 dilution and added at the target concentrations of 25 and 40 ppm.

Lactoside was prepared at a 1:2000 dilution and added at the target concentration of 2.6 ppm.

Results

Table 7 demonstrates that the co-culture of yeast and Z. mobilis shows increased ethanol production over yeast alone. Also, there is a decrease in final glycerol, indicating an improved fermentation yield. Treatment with hop acids along with yeast/Z. mobilis co-culture shows a synergistic increase to ethanol titer compared to yeast alone.

Figure 9:
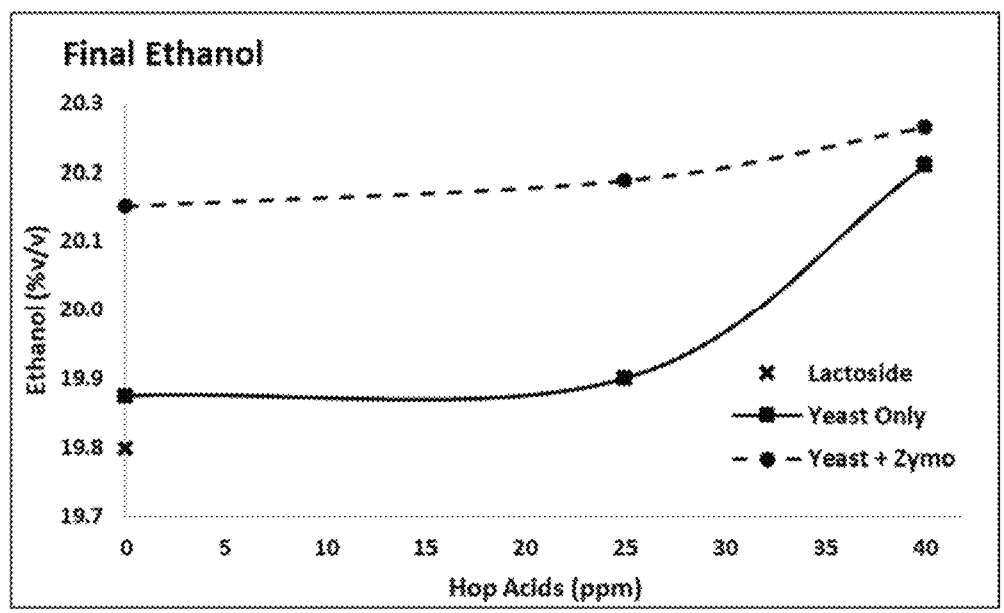
FIG. 9 illustrates the ethanol production after an 88 hour fermentation of Z. mobilis and yeast in the presence of hop acids for antibiotic free fermentation.

FIG. 9 shows how inclusion of increasing amounts of hop acids in fermentations performed with yeast/Z. mobilis co-cultures demonstrated increased ethanol production over ethanol production in the presence of hop acids or traditional antibiotics by yeast only.

TABLE 7

| | \multicolumn{9}{c|}{fermentation products at 88 hours of fermentation} |
| Treatment | ETOH (v/v %) | DP4+ (w/v %) | DP3 (w/v %) | Malt (w/v %) | Gluc (w/v %) | Succ (w/v %) | Lactic (ppm) | Glyc (w/v%) | Acetic (ppm) |
| --- | --- | --- | --- | --- | --- | --- | --- | --- | --- |
| Yeast Only Lactoside | 19.80 | 0.44 | 0.01 | 0.01 | 0.03 | 0.21 | 1467 | 1.04 | 591 |
| Yeast Only 0 ppm Hop acids | 19.87 | 0.44 | 0.01 | 0.01 | 0.03 | 0.19 | 1520 | 1.03 | 511 |
| Yeast Only 25 ppm Hop acids | 19.90 | 0.44 | 0.01 | 0.01 | 0.04 | 0.19 | 1495 | 1.02 | 527 |
| Yeast Only 40 ppm Hop acids | 20.21 | 0.46 | 0.01 | 0.01 | 0.03 | 0.18 | 1565 | 1.03 | 503 |
| Yeast + Zymo 0 ppm Hop acids | 20.15 | 0.44 | 0.01 | 0.01 | 0.05 | 0.17 | 1444 | 0.90 | 674 |
| Yeast + Zymo 25 ppm Hop acids | 20.19 | 0.45 | 0.01 | 0.01 | 0.06 | 0.17 | 1321 | 0.88 | 674 |
| Yeast + Zymo 40 ppm Hop acids | 20.26 | 0.44 | 0.01 | 0.01 | 0.06 | 0.17 | 1373 | 0.88 | 679 |

Example 6: Inclusion of Z. mobilis in Fermentation in the Presence of Protease/Phytase, Cellulase/Xylanase, or all 4 Enzymes Fermentations with yeast and various accessory enzymes were compared to cofermentations with yeast and Z. mobilis and various accessory enzymes.

Preparation of Inoculum

Saccharomyces cerevisiae, as a commercial cream yeast (Novozymes Innova PT), was added to a yeast propagation set up as follows. Ground corn was mixed with "preblend" (a mixture of the waters from various streams that are reused in an ethanol production facility) in an appropriate ratio to obtain slurry (mash) with 35 percent dry solids (including the solids contributed by the preblend water). "Preblend" was used as make up water in these studies to simulate the composition of mash, employing an exemplary embodiment, as it would be in a commercial ethanol production facility. The pH of the corn and "preblend" slurry was approximately 4.5-4.8.

An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase). Urea (50 percent liquor) was added to the slurry to give a final concentration of approximately 1000 ppm urea. The slurry was mixed in 250 milliliter wide mouth bottles at 150 milliliters per bottle. The bottles were covered with a bottle cap with a $\frac{1}{16}$" hole drilled into the top for gas release following addition of enzyme and inoculation of the necessary organisms and placed stationary in a water bath. The fermentation temperature was held constant at 32.2 degrees Celsius for 8 hours. This yeast propagation was then used to inoculate fermentations including yeast at a ratio level of 3-4% total fermentation volume.

ATCC31821 culture (Z. mobilis (ATCC #31821)) was grown in 6% Zymo medium (a growth medium containing 60 grams/Liter Glucose, 10 grams/Liter Yeast extract, and 10 grams/Liter peptone) at 30 degrees Celsius overnight (approximately 18-24 h). This culture was concentrated to an OD600 of 20 in deionized water and used as the inoculum for seed train media at a 1% inoculation level. The seed train media was prepared using ground corn and preblend mixed to a level of 28% solids. Liquefaction was then performed using 0.017% w/w Novozymes Fortiva Revo HPI alpha amylase on an as is corn basis, followed by sterilization at 121 degrees Celsius for 15 minutes. At the time of inoculation, gluco amylase was added to target a dose of 0.05 to 1 AGU/gDS. The seed train was allowed to grow at 30 degrees Celsius for 24 hours, and was then added into fermentation immediately following yeast propagation at approximately 0.7% addition in cultures containing both yeast and Z. mobilis.

Preparation of Mash and Fermentation

Ground corn was mixed with "preblend" (a mixture of the waters from various streams that are reused in an ethanol production facility) in an appropriate ratio to obtain slurry (mash) with approximately 37.5% percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8.

An enzyme blend for raw starch hydrolysis was added to the slurry. The enzyme blend was added to target a dose of 0.005-0.05 FAU-F/g DS (acid fungal amylase) and 0.3-0.5 AGUs/g DS (amyloglucosidase).

All accessory enzyme amounts are expressed as "as is" enzyme preparation. In protease/phytase containing fermentations, DuPont Fermgen 2.5× protease was added at approximately 49 ug/gDS and Optimash Phytase was added at approximately 3 ug/gDS. In cellulase/xylanase containing fermentations, Novozymes NS50243 cellulase was added at approximately 0.4 mg/gDS and Novozymes NS50532 xylanase was added at approximately 0.2 mg/gDS.

Urea (50 percent liquor) was added to the slurry to give a final concentration of approximately 50 ppm urea. The slurry was mixed in 250 milliliter wide mouth bottles at 100 milliliters per bottle. The bottles were covered with a bottle cap with a $\frac{1}{16}$" hole drilled into the top for gas release following addition of enzyme and inoculation of the necessary organisms and placed stationary in a water bath. The fermentation temperature was held constant at 30.6 degrees Celsius for 88 hours. Bottles were mixed well and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Results

The results in Table 9 show ethanol titers and residual starch levels at 88 hours of fermentation. The accessory enzymes each caused a boost in ethanol both with yeast alone and with wildtype Z. mobilis included in the fermentation. The largest boost in ethanol titer was seen with all four enzymes included and also the greatest reduction in starch. In each condition, the ethanol titers for fermentations containing wildtype Z. mobilis were higher than yeast alone.

TABLE 9

88 h Ethanol and Starch.

| | Ethanol (v/v %) | | Starch (dw %) | |
|---|---|---|---|---|
| | Yeast | Yeast + Zymo | Yeast | Yeast + Zymo |
| No accessory enzymes | 20.48 | 20.8 | 12.79 | 12.87 |
| Protease/Phytase | 20.85 | 20.93 | 11.7 | 11.31 |
| Cellulase/Xylanase | 20.63 | 20.81 | 10.46 | 10.04 |
| Protease/Phytase/ Cellulase/Xylanase | 21.04 | 21.11 | 9.14 | 9.16 |

Example 7: Inclusion of Z. mobilis in Fermentation in the Presence of Cellulase and Xylanase Fermentations with yeast in the presence of cellulase and xylanase were compared to fermentations with yeast and Z. mobilis in the presence of cellulase and xylanase.

Preparation of Inoculum

Saccharomyces cerevisiae, (Novozymes Innova PT and Ethanol Red), yeast were grown overnight in YPD medium a growth medium containing 30 grams/Liter Glucose, 10 grams/Liter Yeast extract, and 20 grams/Liter peptone. They were then added to a yeast propagation set up as follows. Ground corn was mixed with "preblend" (a mixture of the waters from various streams that are reused in an ethanol production facility) in an appropriate ratio to obtain slurry (mash) with 26 percent dry solids (including the solids contributed by the preblend water). "Preblend" was used as make up water in these studies to simulate the composition of mash, employing an exemplary embodiment, as it would be in a commercial ethanol production facility. The pH of the corn and "preblend" slurry was approximately 4.5-4.8.

An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase).

Urea (50 percent liquor) was added to the slurry to give a final concentration of approximately 1000 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 32.2 degrees Celsius for 8 hours. This yeast propagation was then used to inoculate fermentations including yeast at a ratio level of 3-4% total fermentation volume.

The wild type ATCC31821 culture (Z. mobilis) was grown in 6% Zymo medium (a growth medium containing 60 grams/Liter Glucose, 10 grams/Liter Yeast extract, and 10 grams/Liter peptone) at 30 degrees Celsius overnight (approximately 18-24 h). This culture was concentrated to an OD600 of 20 in deionized water and used as the inoculum for the mash at a 1% inoculation level into fermentation immediately following yeast propagation addition in cultures containing both yeast and Z. mobilis.

Preparation of Mash and Fermentation

Ground corn was mixed with "preblend" (a mixture of the waters from various streams that are reused in an ethanol production facility) in an appropriate ratio to obtain slurry (mash) with 32-38% percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8.

An enzyme blend for raw starch hydrolysis was added to the slurry. The enzyme was added to target a dose of 0.005-0.05 FAU-F/g DS (acid fungal amylase) and 0.3-0.5 AGUs/g DS (amyloglucosidase).

In bottles containing cellulase and xylanase, approximately 1 mg "as is" enzyme/g DS was used each of NS50532 Xylanase from Novozymes and CTEC3 Cellulase from Novozymes. Urea (50 percent liquor) was added to the slurry to give a final concentration of approximately 300 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 30.6 degrees Celsius for 88 hours. Bottles were mixed well and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Results

The results in Table 10 show ethanol titers and residual starch levels at 88 hours of fermentation. These levels of cellulase and xylanase enable a 80% and 48% reduction in final starch with InnovaPT and Ethanol Red respectively. The inclusion of Z. mobilis in these fermentations enables the reduction of residual starch by 81% and 53% in these two yeasts respectively when compared to a no enzyme and no bacterial inclusion control. Ethanol titers were boosted in InnovaPT fermentations by 2.9% in the presence of cellulase and xylanase, and 3.8% when Z. mobilis was included. In Ethanol Red fermentations, titers were increased by 3% in the presence of cellulase and xylanase and 5.7% when Z. mobilis was included.

TABLE 10

88 Hour Ethanol and Residual Starch

| Yeast | Bacteria | Cellulase/ Xylanase? | 88 h ETOH (v/v %) | 88 h Residual Starch % |
|---|---|---|---|---|
| Novozymes InnovaPT | None | No | 15.36 | 4.1 |
| | None | Yes | 15.8 | 0.82 |
| | WT Z. mobilis | Yes | 15.94 | 0.79 |
| Ethanol Red | None | No | 14.88 | 6.22 |
| | None | Yes | 15.33 | 3.23 |
| | WT Z. mobilis | Yes | 15.73 | 2.95 |

Example 8: Inclusion of Z. mobilis in Fermentation in the Presence of Protease

Fermentations with yeast in the presence of protease were compared to cofermentations with yeast and Z. mobilis in the presence of protease.

Preparation of Inoculum

Saccharomyces cerevisiae, as a commercial yeast cream, was added to a yeast propagation set up as follows. Ground corn was mixed with "preblend" (a mixture of the waters from various streams that are reused in an ethanol production facility) in an appropriate ratio to obtain slurry (mash) with 35 percent dry solids (including the solids contributed by the preblend water). "Preblend" was used as make up water in these studies to simulate the composition of mash, employing an exemplary embodiment, as it would be in a commercial ethanol production facility. The pH of the corn and "preblend" slurry was approximately 4.5-4.8.

An enzyme blend for raw starch hydrolysis was added to the slurry. The enzyme blend was added to target a dose of 0.004-0.05 FAU-F/g DS (acid fungal amylase) and 0.2-0.4 AGUs/g DS (amyloglucosidase).

Urea (50 percent liquor) was added to the slurry to give a final concentration of approximately 1000 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 32.2 degrees Celsius for 8 hours. This yeast propagation was then used to inoculate fermentations including yeast at a ratio level of 3-4% total fermentation volume.

ATCC31821 culture (Z. mobilis) was grown in 6% Zymo medium (a growth medium containing 60 grams/Liter Glucose, 10 grams/Liter Yeast extract, and 10 grams/Liter peptone) at 30 degrees Celsius overnight (approximately 18-24 h). This culture was concentrated to an OD600 of 20 in deionized water and used as the inoculum for the mash at a 1% inoculation level into fermentation immediately following yeast propagation addition in cultures containing both yeast and Z. mobilis.

Preparation of Mash and Fermentation

Ground corn was mixed with "preblend" (a mixture of the waters from various streams that are reused in an ethanol production facility) in an appropriate ratio to obtain slurry (mash) with approximately 38% percent dry solids (including the solids contributed by the preblend water). "Preblend" was used as make up water in these studies to simulate the composition of mash, employing an exemplary embodiment of the present disclosure, as it would be in a commercial ethanol production facility. The pH of the corn and "preblend" slurry was approximately 4.8.

An enzyme blend for raw starch hydrolysis was added to the slurry. The enzyme blend was added to target a dose of 0.005-0.05 FAU-F/g DS (acid fungal amylase) and 0.3-0.5 AGUs/g DS (amyloglucosidase).

In protease containing samples, approximately 53 ug/gDS "as is" Novozymes ProEx protease or DuPont Fermgen 2.5x protease was added.

Urea (50 percent liquor) was added to the slurry to give a final concentration of approximately 50 ppm urea. The slurry was mixed in 100 milliliter wide mouth bottles at 60 milliliters per bottle. The bottles were covered with a bottle cap with a 1/16" hole drilled into the top for gas release following addition of enzyme and inoculation of the necessary organisms and placed stationary in a water bath. The fermentation temperature was held constant at 30.6 degrees Celsius for 88 hours. Bottles were mixed well and samples were withdrawn at various intervals during the course of fermentation and analyzed for sugars, organic acids and ethanol using high performance liquid chromatography (HPLC) with a Concise Separations Coregel ORH 801 FA column paired with a Coregel ORH 801 guard column.

Results

Figure 10:
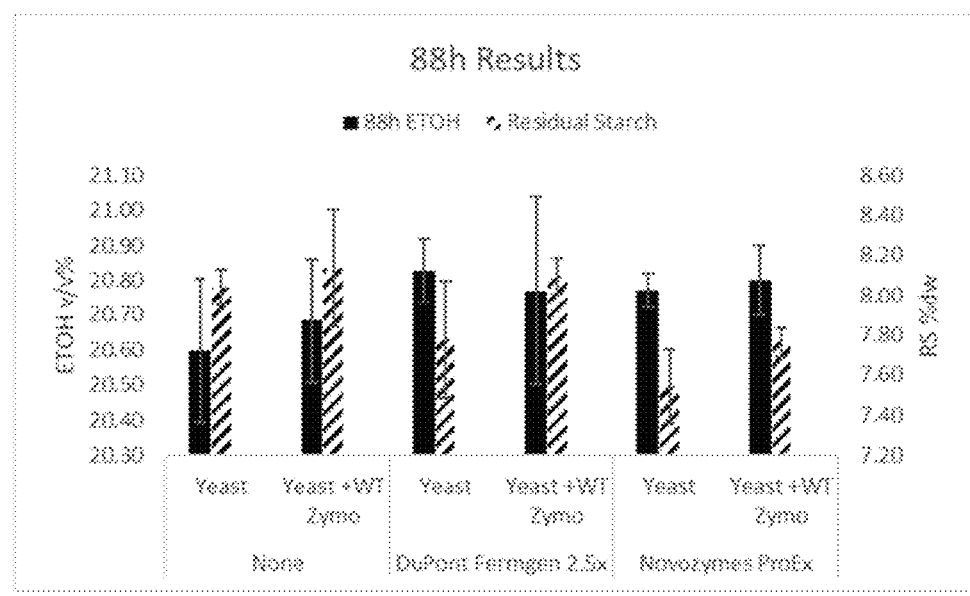
FIG. 10 shows ethanol titers and residual starch levels at 88 hours of fermentation with Z. mobilis and yeast in the presence of protease.

The results in FIG. 10 show ethanol titers and residual starch levels at 88 hours of fermentation. The Z. mobilis containing fermentations generally produced more ethanol from less residual starch as indicated by equal or higher ethanol titers, with more residual starch remaining. The presence of protease helped to increase ethanol titers, and decrease residual starch, especially in the case of Novozymes Proex protease.

What is claimed is:

1. A method of ethanol fermentation, the method comprising inoculating a feedstock with S. cerevisiae and Z. mobilis, and fermenting the feedstock in the absence of one or more antibiotics to produce ethanol and fermentation solids, wherein the feedstock is a bacterially contaminated grain mash.

2. The method of claim 1, wherein the feedstock is inoculated with Z. mobilis prior to or during S. cerevisiae propagation.

3. The method of claim 1, wherein the Z. mobilis is inoculated with the S. cerevisiae in a propagator.

4. The method of claim 1, wherein the feedstock is inoculated with Z. mobilis prior to or during fermentation.

5. The method of claim 1, wherein the Z. mobilis is added to a fermenter before or after S. cerevisiae propagation is added to the fermenter.

6. The method of claim 1, wherein levels of lactic acid bacteria during fermentation are decreased by at least 5% relative to a fermentation in the absence of Z. mobilis.

7. The method of claim 1, wherein little or no fusel oils are present in the fermentation solids.

8. The method of claim 1, wherein the glycerol content of the fermentation solids is reduced relative to a fermentation in the absence of Z. mobilis.

9. The method of claim 1, wherein ethanol yield is increased relative to a fermentation in the absence of Z. mobilis.

10. The method of claim 1, wherein yeast numbers are decreased after fermentation relative to a fermentation in the absence of Z. mobilis.

11. The method of claim 1, wherein hop acids are added to the fermentation.

12. The method of claim 1, wherein protease, phytase, cellulase, xylanase, or any combination thereof is added to the fermentation.

13. The method composition of claim 11, wherein the hop acids are present in an amount from about 25 ppm to 40 ppm.

14. The method of claim 1, wherein Z. mobilis is added to a raw starch hydrolysis reaction to reduce lactic acid bacterial contamination.

* * * * *